United States Patent

Nedenskov

[11] 3,970,645
[45] July 20, 1976

[54] 1,4-BENZODIAZEPINE DERIVATIVE

[75] Inventor: Poul Nedenskov, Birkerod, Denmark

[73] Assignee: Aktieselskabet Grindstedvaerket, Arhus, Denmark

[22] Filed: Aug. 15, 1974

[21] Appl. No.: 497,771

[30] Foreign Application Priority Data
Aug. 24, 1973 United Kingdom............... 40259/73

[52] U.S. Cl........................... 260/239.3 D; 424/244
[51] Int. Cl.²........................................ C07D 243/24
[58] Field of Search.............................. 260/239.3 D

[56] References Cited
UNITED STATES PATENTS
3,299,053  1/1967  Archer et al.................. 260/239.3 D
3,567,710  3/1971  Fryer et al. ..................... 260/239.3 D OTHER PUBLICATIONS
Calvenor "Amine Oxides" in Reviews of Pure and Applied Chemistry, vol. 3 (1953).

Primary Examiner—Henry R. Jiles
Assistant Examiner—Robert T. Bond
Attorney, Agent, or Firm—Lawrence Rosen; E. Janet Berry

[57] ABSTRACT

The invention relates to new 1,4-benzodiazepine derivatives of the formula

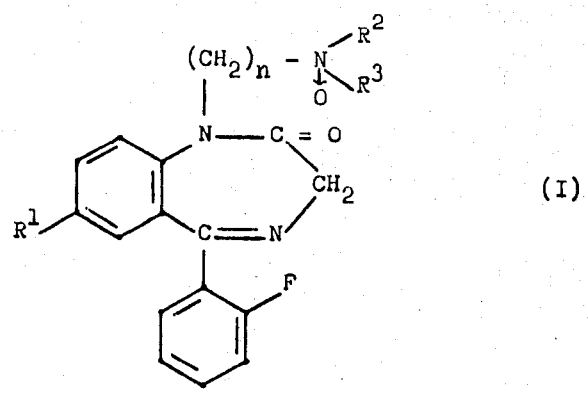

(I)

wherein $R^1$ is hydrogen, halogen, or the trifluoromethyl group, $R^2$ and $R^3$ are alkyl groups, and $n$ is an integer from 1 to 4, and acid addition salts thereof, the compounds and salts being soluble in water, and having analgetic, sedative, and narcosis potentiating properties.

1 Claim, No Drawings

1,4-BENZODIAZEPINE DERIVATIVE

This invention relates to new 1,4-benzodiazepine derivatives, to their acid addition salts with pharmaceutically acceptable acids, and to their production.

The benzodiazepines of the invention are represented by the following formula

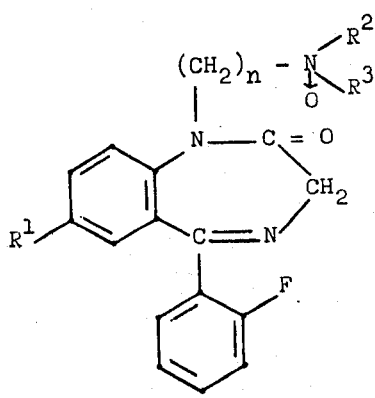

(I)

wherein $R^1$ represents hydrogen, halogen or the trifluoromethyl group, $R^2$ and $R^3$ represent alkyl groups of 1–4 carbon atoms, and $n$ is an integer from 1 to 4.

If $R^1$ is halogen, it is preferably chlorine.

Examples of the alkyl groups represented by $R^2$ and $R^3$ are methyl, ethyl, isopropyl, and n-butyl, preferably ethyl.

The compounds of the invention and their acid addition salts with physiologically innocuous acids have valuable analgetic, sedative, and narcosis potentiating properties, making them suitable for therapeutic use.

Moreover, the free bases are soluble in water, making them particularly valuable in treatment of babies and small children, and also ensuring a rapid effect upon administration.

They are produced, according to the invention, by oxidizing a compound of the formula

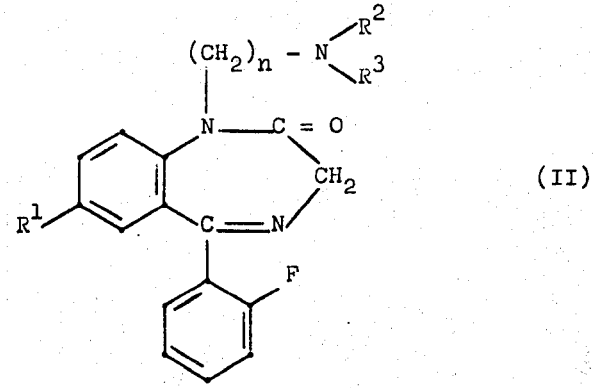

(II)

wherein $R^1$, $R^2$, $R^3$, and $n$ are as hereinbefore defined, with a peroxidic compound.

The preferred peroxidic compound is m-chloroperoxybenzoic acid.

The following scheme of reaction is illustrative of the production

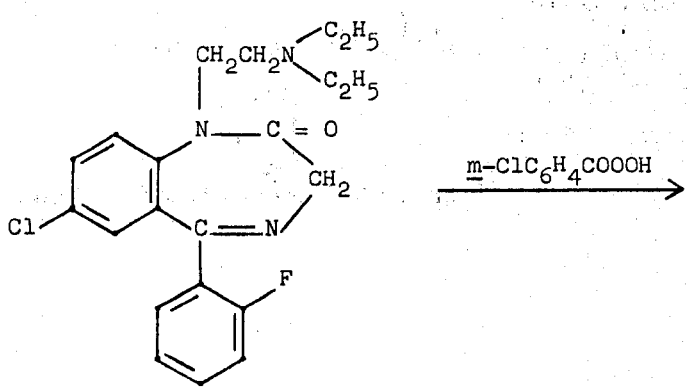 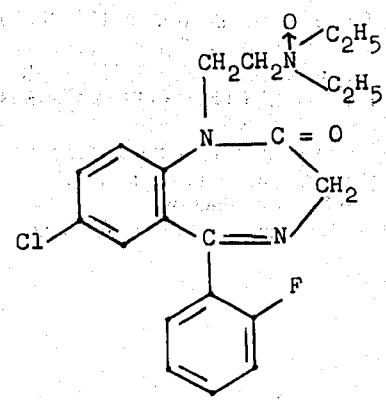

The starting materials of formula II are known compounds.

The advantages shown by the compounds of the invention have been demonstrated in tests comparing the presently preferred compound of the invention, viz. 7-chloro-1-[2-(diethylaminoxide)-ethyl]-5-(o-fluorophenyl)-1,3-dihydro-2H-1,4-benzodiazepin-2-one, hereinafter referred to as CK 687, with the corresponding starting compound, known under the non-proprietary name Flurazepam, using mice as test animals.

The $LD_{50}$ of CK 687 proved to be more than 1000 mg/kg by oral administration, and 330 mg/kg by intravenous injection as compared with 600 mg/kg and 70 mg/kg, respectively for Flurazepam.

Oral administration of 100 mg/kg resulted in an equally strong sedative effect during 11 hours for both of the compared compounds, the effect still being noticeable after 24 hours.

Whereas Flurazepam gave an unmistakable muscle-relaxing effect by intraperitoneal administration of 175 mg/kg, no such effect could be noted for CK 687 in doses up to 375 mg/kg.

The narcosis-potentiating effect as measured by the duration of sleeping was more than 100% increase of the sleeping time by administering a dose of 50 mg/kg either orally or intraperitoneally, the effect being somewhat stronger for Flurazepam than for CK 687.

EXAMPLE

The hydrochloride of 7-chloro-1-(2-diethylaminoethyl)-5-(o-fluorophenyl-1,3-dihydro-2H-1,4-benzodiazepin-2-one (13.8 g, 0.0300 mole) was dissolved in water (60 ml), and 3N sodium hydroxide (24 ml, 0.072 mole) was added. The oil which separated was extracted with ether (60+60+60 ml), and the combined organic phases were dried over magnesium sulphate and evaporated to dryness from a water bath (50°C, 10 mm Hg).

The residual oil (11.64 g) was dissolved in chloroform (225 ml) and stirred at 0°C, and 85% m-chloroperoxybenzoic acid (6.75 g, 0.0333 mole) was added in one portion. The resulting solution was stirred at 0°C for 1 hour.

The solution was then passed through a column of alkaline alumina (300 g) and eluted with a 3:2 mixture of chloroform and methanol. The main fraction from the column was evaporated by dryness from a water bath (70°C, 10 mm Hg) and allowed to crystallize in a humid atmosphere. The crystals were washed with ether (25+25+25 ml) and dried (50°C, 10 mm Hg) to give 10.86 g of 7-chloro-1-[2-(diethylaminooxide)-ethyl]-5-(o-fluorophenyl)-1,3-dihydro-2H-1,4-benzodiazepin-2-one (CK 687) as white crystals. The product was crystallized twice from benzene (150 ml) in a humid atmosphere and dried (50°C, 10 mm Hg) to give 8.42 g of the dihydrate of CK 687 (64%) as white crystals with m.p. 109°–110°C (dec.).

Calculated for $C_{21}H_{23}ClFN_3O_2 \cdot 2H_2O$ (439.9): C 57.3 H 6.2 N 9.5 Cl 8.0 $H_2O$ 8.2. Found: C 57.5 H 6.3 N 9.6 Cl 8.1 $H_2O$ 8.3.

The solubility of the compound in water is higher than 20% at room temperature.

What is claimed is:
1. A compound of the formula:

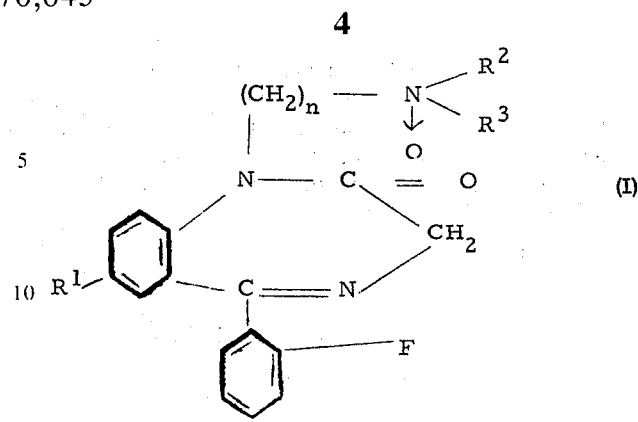

wherein $R^1$ is chloro, $R^2$ and $R^3$ are ethyl, and $n$ is 2.

* * * * *